United States Patent
Hollingsworth et al.

(10) Patent No.: US 6,590,121 B2
(45) Date of Patent: Jul. 8, 2003

(54) PROCESS FOR THE PREPARATION OF 1,5-DIDEOXY-1,5-IMINO HEXITOLS FROM OXIMES OR IMINES

(75) Inventors: Rawle I. Hollingsworth, Haslett, MI (US); Gabriela Pistia-Brueggeman, Lansing, MI (US)

(73) Assignee: Board of Trustees operating Michigan State University, East Lansing, MI (US)

( * ) Notice: Subject to any disclaimer, the term of this patent is extended or adjusted under 35 U.S.C. 154(b) by 54 days.

(21) Appl. No.: 09/970,866

(22) Filed: Oct. 4, 2001

(65) Prior Publication Data

US 2002/0016447 A1 Feb. 7, 2002

Related U.S. Application Data

(62) Division of application No. 09/819,581, filed on Mar. 28, 2001.
(60) Provisional application No. 60/193,554, filed on Mar. 31, 2000.

(51) Int. Cl.⁷ ................................................ C07C 69/34
(52) U.S. Cl. ....................................................... 560/196
(58) Field of Search ......................................... 560/196

(56) References Cited

U.S. PATENT DOCUMENTS

| | | |
|---|---|---|
| 4,611,058 A | 9/1986 | Koebernick |
| 4,634,765 A | 1/1987 | Liu |
| 4,806,650 A | 2/1989 | Schroder et al. |
| 4,837,237 A | 6/1989 | Rohrschneider |
| 4,908,439 A | 3/1990 | Anzeveno |
| 4,940,705 A | 7/1990 | Boshagen et al. |
| 4,957,926 A | 9/1990 | Jacob et al. |
| 5,227,479 A | 7/1993 | Anzeveno et al. |
| 5,250,545 A | 10/1993 | Tsuruoka et al. |
| 5,610,039 A | 3/1997 | Grabner et al. |
| 5,643,888 A | 7/1997 | Rohrschneider |
| 5,695,969 A | 12/1997 | Grabner |

OTHER PUBLICATIONS

Inouye, et. al., "Structure and synthesis of Nojirimycin", Tetrahedron, vol. 23, pp. 2125–2144, 1968.*
Shilvock, J.P., et al., Tetrahedron Lett., 37 8569–8572 (1996).
Rajanikanth, D.G., et al., J. Chem. Sco. Perkin Trans. I 2151–2152 (1992).
Hussain, A.,, et al., Tetrahedron 49 2123–2130 (1993).
Defoin, A., et al., Tetrahedron Lett. 34 4327–4330 (1997).
Defoin, A., et al., Tetrahedron 53 13769–13782 (1997).
Defoin, A.,, et al., Tetrahedron Lett. 35 5653–5656 (1994).
Fleet, G.W.J., et al., Tatrahedron Lett. 29 2871–2874 (1988).
Fleet, G.W.J., et al., Tetrahedron 45 327–336 (1989).
Takahashi, S., et al., Chem., Lett 21–24 (1992).
Takahashi, S., et al., J. Chem. Soc., Perkin Trans. I, 607–612 (1997).
Hendry, D., et al., Tetrahedron Lett. 28 4597–4600 (1987).
Hendry, D., et al., Tetrahedron Lett. 28 4601–4604 (1987).
Straub, A., et al., J. Org. Chem. 55 3926–3932 (1990).
Delinck, D.L., et al., Tetrahedron Lett. 31 3093–3096 (1990).
Look, G.C., et al., Acc. Chem. Res. 26 182–190 (1993).

(List continued on next page.)

*Primary Examiner*—Alan L. Rotman
*Assistant Examiner*—Binta Robinson
(74) *Attorney, Agent, or Firm*—Ian C. McLeod

(57) ABSTRACT

A process for the preparation of 1,5-dideoxy-1,5-imino hexitols of a hexose sugars from novel hydroxyl protected oxime intermediates. The process includes formation of a lactam which is reduced to the hexitol. The hexitols are useful as drugs.

3 Claims, 3 Drawing Sheets

OTHER PUBLICATIONS

Kajimoto, T., et al., J. Am. Chem. Soc. 113 6678–6680 (1991).

Truscheit, E., et al., Angew. Chem. Int. Ed. Engl. 20 744–761 (1981).

Dennis, J.W., Cancer Res. 46 5131–5136 (1986).

Humphries J.J., et al Cancer Res. 46 5215–5222 (1986).

Walker, B.D., et al., Proc. Natl. Acad. Sci. USA 84 8120–8124 (1987).

Karpas, A., et al., Proc. Natl. Acad. Sci. USA 85 9229–9233 (1988).

Fleet, G.W.J., et al., FEBS Lett. 237 128–132 (1988).

Tsuda, Y., et al., Heterocycles, 27 63–66 (1988).

Inouye, S., et al., Tetrahedron 23 2125–2144 (1968).

Vasella, A., et al., Helv. Chim. Acta 65 1134–1144 (1982).

Ikota, N., et al., Heterocycles 46 637–643 (1997).

Paulsen, H., et al., Chem. Ber 100 802–815 (1967).

Rudge, A.J., et al., Angew. Chem. Int. Ed. Engl. 33 2320–2322 (1994).

Behling, J., et al., Synth. Commun. 21 1383–1386 (1991).

Kinast, G., et al., Angew. Chem. Int. Ed. Engl. 20 805–806 (1981).

Pederson, R.L., et al., Tetrahedron Lett. 29 4645–4648 (1988).

Osten, C.H., et al., J. Am. Chem. Soc. 111 3924–3927 (1989).

Kajmioto, T., et al., J. Am. Chem. Soc. 113 6187–6196 (1991).

* cited by examiner

SCHEME 1

SCHEME 2

PROCESS FOR THE PREPARATION OF 1,5-DIDEOXY-1,5-IMINO HEXITOLS FROM OXIMES OR IMINES

CROSS-REFERENCE TO RELATED APPLICATIONS

"This application is a divisional of application(s) application Ser. No. 9/819,581 filed on Mar. 28, 2001."

This application claims priority to Provisional Application No. 60/193,554, filed Mar. 31, 2000.

STATEMENT REGARDING FEDERALLY SPONSORED RESEARCH OR DEVELOPMENT

None.

BACKGROUND OF THE INVENTION (1) Field of the Invention

The present invention relates to multistep synthesis of a 1,5-dideoxy-1,5-imino hexitol from a ketoaldonic acid methyl ester of a hexose sugar with protected hydroxyl groups and to novel intermediates. In particular the present invention relates to processes which enable the production of novel intermediates to the hexitol and in particular, a ketoaldonic acid methyl ester oxime or alkylimine, which forms the ring structure of the hexitol by alternate routes.

(2) Description of Related Art

Over the last three decades there has been a continued interest in natural and synthetic imino-sugars because of their high potency as glycosidase inhibitors ((a) Grabner, R. W., et al., U.S. Pat. No. 5,695,969; (b) Boshagen, H., et al., U.S. Pat. No. 4,940,705; (c) Shilvock, J. P., et al., Tetrahedron Lett., 37 8569–8572 (1996); (d) Rajanikanth, D. B., et al., J. Chem. Soc. Perkin Trans. I 2151–2152 (1992); (e) Hussain, A., et al., Tetrahedron, 49 2123–2130 (1993); (f) Defoin, A., et al., Tetrahedron Lett. 34 4327–4330 (1997); (g) Defoin, A., et al., Tetrahedron 53 13769–13782 (1997); (h) Defoin, A., et al., Tetrahedron Lett. 35 5653–5656 (1994); (i) Fleet, G. W. J., et al., Tetrahedron lett. 29 2871–2874 (1988); (j) Fleet, G. W. J., et al., Tetrahedron 45 327–336 (1989); (k) Takahashi, S., et al. Chem. Lett. 21–24 (1992); (l) Takahashi, S., et al., J. Chem. Soc., Perkin Trans. I, 607–612 (1997); (m) Hendry, D., et al., Tetrahedron Lett. 28 4597–4600 (1987); (n) Hendry, D., et al., Tetrahedron Lett. 28 4601–4604 (1987); (o) Straub, A., et al., J. Org. Chem. 55 3926–3932 (1990); Delinck, D. L., et al., Tetrahedron Lett. 31 3093–3096 (1990); (r) Look, G. C., et al., Acc. Chem. Res. 26 182–190 (1993); (s) Kajimoto, T., et al., J. Am. Chem. Soc. 113 6678–6680 (1991)). Glycosidases catalyze the hydrolysis of glycosidic linkages and are the key enzymes in the degradation of complex carbohydrates. One of their main metabolic roles is the conversion of complex non-absorbable carbohydrates into absorbable mono- or oligosaccharides (Truscheit, E., et al., Angew. Chem. Int. Ed. Engl. 20 744–761 (1981)). The rapid action of these enzymes can lead, however, to undesirable elevations in blood glucose in diabetes. Iminosugars have been shown to act as glycosidase inhibitors and to retard and regulate the intestinal carbohydrate digestion. They are therefore excellent drug candidates for diabetes therapy (Liu, P. S., U.S. Pat. No. 4,634,765 (1987)). An even more exciting potential use of iminosugars is in the treatment of cancer and viral diseases (Rohrschneider, L. R., et al., U.S. Pat. No. 4,837,237 (1989)). It has been shown that modification of oligosaccharide structures may alter metastatic capacity of cancer cells and 1,5-diimino-1,5-dideoxyglucitol (deoxynojirimycin) (1) (Tsuruoka, T., et al., U.S. Pat. No. 5,250,545 (1993)) swainsonine (2) (Dennis, J. W., Cancer Res. 46 5131–5136 (1986)) and castanospermine (3) (Humphries, M. J., et al., Cancer Res. 46 5215–5222 (1986)) (FIG. 1.) can markedly inhibit metastasis of cancer cells. They might, therefore, be used for the effective treatment of cancer.

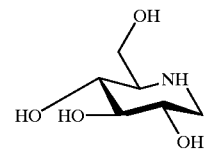

1

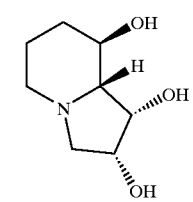

2

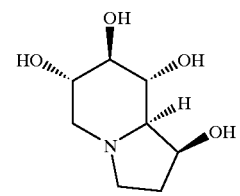

3

N-Butyl-deoxynojirimyciin shows excellent activity against herpes virus (Jacob, G. S., et al., U.S. Pat. No. 4,957,926 (1990)) whilst having low cyto-toxicity and no inhibitory effect on the growth of normal cells. The greatest prospect for the use of iminosugars as drugs is probably for the treatment of AIDS. Glycosidase inhibitors prevent the processing of N-linked complex oligosaccharides. This results in the disruption of the synthesis of viral coat glycoproteins such as the critical one called gp120. This supposedly leads to the loss of recognition by the CD-4 receptor of the target cell with concomitant reduction of syncytia formation resulting in the reduction of virus infectivity and the inhibition of viral replication (Walker, B. D., et al., Proc. Natl. Acad. Sci. USA 84 8120–8124 (1987); Karpas, A., et al., Proc. Natl. Acad. Sci. USA 85 9229–9233 (1988); Fleet, G. W. J., et al., FEBS Lett. 237 128–132 (1988)). Clinical trials have been launched for N-Butyl-deoxynojirimycin (Rohrschneider, L. R., U.S. Pat. No. 5,643,888 (1997)). The iminosugars that have been the most investigated are deoxynojirimycin ((a) Schroder, T., et al., U.S. Pat. No. 4,806,650 (1989); (b) Koebernick, W., U.S. Pat. No. 4,611,058 (1986); (c) Anzeveno, P. B., et al. U.S. Pat. No. 5,227,479 (1993); (d) Anzeveno, U.S. Pat. No. 4,908,439 (1990); (e) Tsuda, Y., et al., Heterocycles, 27 63–66 (1988); (f) Inouye, S., et al., Tetrahedron 23 2125–2144 (1968); (g) Vasella, A., et al., Helv. Chim. Acta 65 1134–1144 (1982); Ikota, N., et al., Heterocycles 46 637–643 (1997); (i) Paulsen, H., et al., Chem. Ber 100 802–815 (1967); (j) Rudge, A. J., et al., Angew. Chem. Int. Ed. Engl. 33 2320–2322 (1994); (k) Behling, J., et al., Synth. Commun. 21 1383–1386 (1991); (l) Kinast, G., et al., Angew. Chem. Int. Ed. Engl. 20 805–806 (1981); (m) Pederson, R. L., et al., Tetrahedron Lett. 29 4645–4648 (1988); (n) Osten, C. H., et al., J. Am. Chem. Soc. 111 3924–3927 (1989)) and its N-alkyl analogues (Grabner, R. W., et al., U.S. Pat. No. 5,610,039

(1997); U.S. Pat. No. 4,806,650; U.S. Pat. No. 4,611,058; U.S. Pat. No. 4,940,705).

The chemical synthesis of nojirimycin derivatives are generally too involved and not suitable for commercial applications. The chemo-microbiological method patented by Grabner (U.S. Pat. No. 5,695,969; U.S. Pat. No. 5,610, 039)) provides an elegant method for transforming a sugar into its imino-derivative by reductive animation of a 5-keto aldose obtained by bacterial oxidation of glucose. The method is in particular however, not applicable to the D-galacto derivatives of the present invention.

Other related patents are: U.S. Pat. Nos. 5,227,479, 5,250, 545, 5,695,969, 4,957,926, 4,908,439 and 4,634,765.

SUMMARY OF INVENTION

The present invention relates to a process for the preparation of an aldonic-5-oxime methyl ester of a hexose sugar which has protected hydroxyl groups which comprises:

(a) reacting a ketoaldonic acid methyl ester of the sugar with the protected hydroxyl groups with a an alkylamine or hydroxylamine acid salt in an organic solvent with a tertiary amine to react with an acid generated in the reaction at a temperature of about 60° C. or less to produce the oxime methyl ester in a reaction mixture; and (b) separating the oxime methyl ester from the reaction mixture.

The present invention also relates to a a process for the preparation of methyl 2,3,4,6-tetra-O-acetyl-5-hexulosonic acid oxime which comprises:

(a) reacting methyl 2,3,4,6 tetra-O-acetyl-5-hexulosonic acid methyl ester with hydroxylamine hydrochloride in a first organic solvent with a tertiary amine to react with an acid generated in the reaction mixture at a temperature of between about −10 and 60° C.;

(b) introducing the reaction mixture into water containing ice;

(c) extracting the oxime from the reaction mixture with a second organic solvent for the oxime; and (d) separating the oxime from the second solvent.

Further, the present invention relates to a process for the preparation of an aldonic acid hydrazide oxime of a hexose sugar with protected hydroxyl groups which comprises:

(a) reacting an aldonic acid-5-oxime or alkylimine methyl ester of the sugar with the protected hydroxyl groups with anhydrous hydrazine in an organic solvent at less than about 30° C. to produce the hydrazide oxime; and (b) separating the hydrazide oxime of the sugar from the reaction mixture.

The present invention also relates to a process for the preparation of the 5-lactam of a hexose sugar which has hydroxyl groups which comprises:

(a) reacting an aldonic acid methyl ester oxime or alkylimine of the sugar with the protected hydroxyl groups with hydrogen and a hydrogenation catalyst in an acidic solvent at a temperature between about 20 and 80° C. and at a pressure between about 200 and 400 psi of the hydrogen to produce the acid lactam of the sugar in a reaction mixture; and (b) separating the lactam from the mixture.

The present invention also relates to a process for the preparation of a 1,5-imino-1,5-dideoxyhexitol which comprises:

(a) reacting a 5-imino-5-deoxyhexonic acid lactam of a hexose sugar which has hydroxyl groups with a reducing agent in a solvent at a temperature between about 0° and 80° C. to produce the 1,5-imino-1,5-dideoxyhexitol in a reaction mixture; and (b) separating the imino 1,5-imino-1,5-dideoxyhexitol from the reaction mixture.

The present invention also relates to a process for the preparation of 1,5-imino,-1,5-dideoxy hexitol with or without the protected hydroxyl groups which comprises:

(a) reacting an acid ester or a hydrazide of a 5-hexulosonic acid oxime or alkylimine with or without the protected hydroxyl group with hydrogen and a hydrogenation catalyst in an acidic solvent at a temperature between about 20 and 80° C. and a pressure between about 200 and 400 psi to form a 5-imino-5-deoxyaldonic acid lactam; and (b) reducing, if necessary deprotecting the hydroxyl groups, the lactam with a reducing agent to form the 1,5-dideoxy-1,5-imino hexitol.

The present invention relates to a process for the preparation of 1,5-imino,-1,5-6-trideoxy hexitol as a product which comprises:

(a) reacting methyl-2,3,4,6-tetra-O-acetyl-5-hexulosonic acid oxime with hydrogen and a hydrogenation catalyst at a temperature between about 20 and 80° C. and a pressure between about 200 and 400 psi in an acidic solvent to form a 1,5,6-triacetoxy acid lactam;

(b) reducing and deacetylating the lactam with a reducing agent to form the 1,5-imino hexitol.

The present invention relates to a process for producing a 1,5-imino hexitol which comprises:

(a) reacting an aldonic acid hydrazine-5-oxime or alkylimine with a reducing agent in an organic solvent at a temperature between about 20 and 80° C. to produce the 1,5imino hexitol in a reaction mixture; and (b) separating the 1,5-imino hexitol from the reaction mixture.

The present invention relates to methyl-2,3,4,6-tetra-O-acetyl-L-arabino-5-hexulosonic acid oxime; methyl-2,3,4,6-tetra-O-acetyl-D-xylo-5-hexulosonic acid oxime; tri-o-acetyl-5-amino-5,6-dideoxy-D-gluconic acid lactam; methyl-2,3,4,6-tetra-O-acetyl-L-xylo-5-hexulosonic acid hydrazide oxime; and L-xylo-5-hexulosonic acid hydrazide.

DESCRIPTION OF PREFERRED EMBODIMENTS

Figure 1:
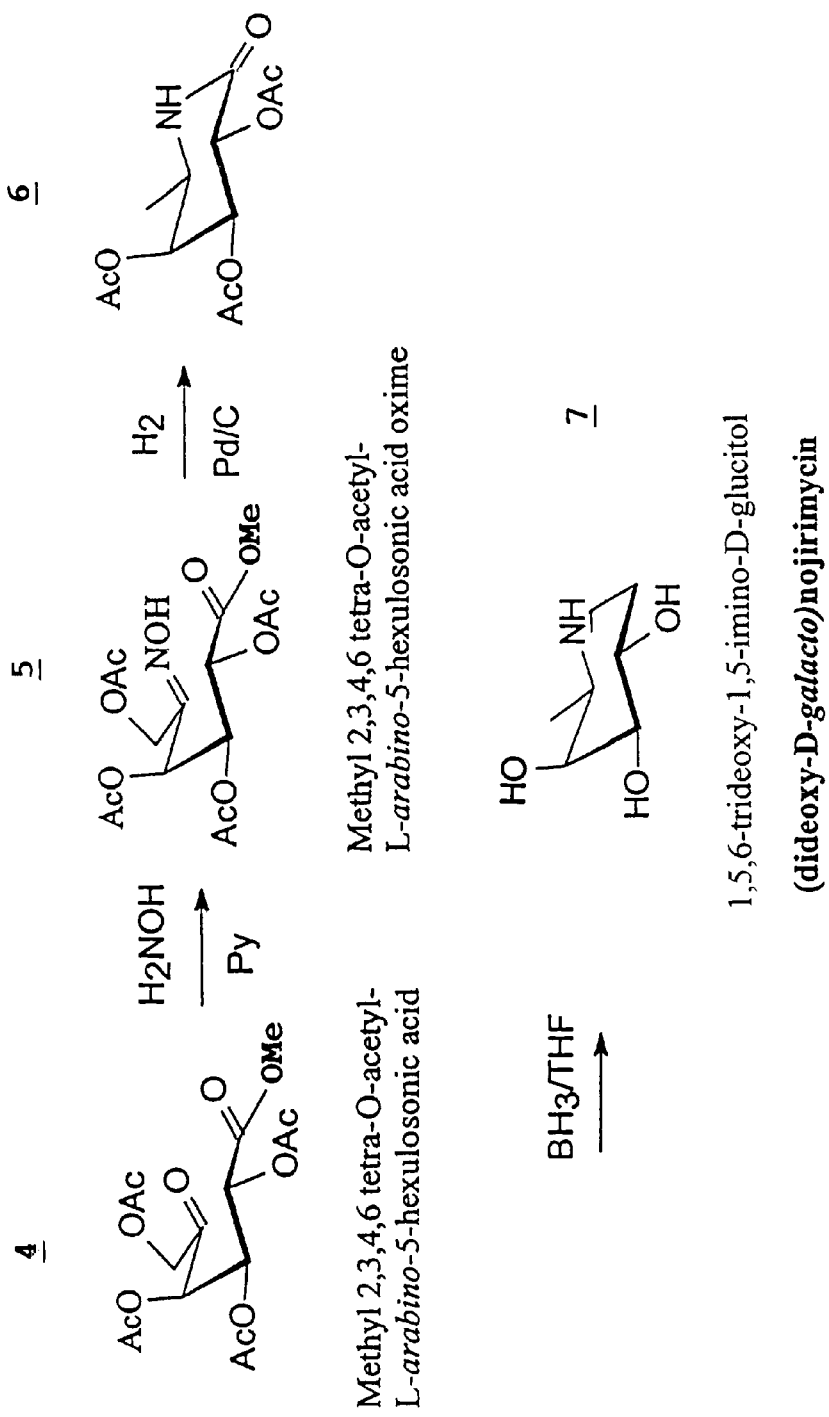
FIG. 1 is a drawing showing the schematic reactions of Examples 1 and 2. The numbers are for the structures of the compounds of these Examples.

In particular, the present invention relates to methyl-2,3, 4,6-tetra-O-acetyl-L-arabino-5-hexulosonic acid oxime 5 (FIG. 1) as an intermediate for the synthesis of D-dideoxy galacto nojirimycins 7. The present invention provides a method for the preparation of 1,5-imino-1,5-dideoxy and 1,5,6-triteoxy alditols with the D-galacto configurations starting from β-glactosides via hexulosonic acid oximes which have not been reported before now. The procedure is especially valuable because of its high stereoselectivity and straightforwardness. The key steps are the reduction of the oxime derivatives to the lactams which is then further reduced to the target compounds. The C6 position can be deoxygenated during the reduction if it bears an acetoxy group. The trideoxy imino sugars are then produced. Deacetylation prior to oxime reduction gives the dideoxy compounds.

The present invention provides a simple access to D-galactonojirimycins from the new oxime intermediate methyl 2,3,4,6-tetra-O-acetyl-L-arabino-5-hexulosonic acid oxime 5. The method also allows access to the 5-amino-5-deoxy-D-galacturonic acid δ-lactams. This also is not known before now although the gluco-isomer has been made by the oxidation of nojirimycin (Kajimoto, T., et al., J. Am. Chem. Soc. 113 6187–6196 (1991)). In this method, the ketoaldonic acid methyl ester is converted to the previously unreported oxime which is then reduced to the amine which cyclizes to give the lactam. The lactam is reduced to the imino sugar by borane or a metal hydride reagent. (Scheme 1). Despite the formation of both the cis- and trans oximes, no L-derivatives are formed Reduction of the peracetylated oxime leads to deoxygenation of the 6 position to give the tri-deoxydiiminoalditol (dideoxy-D-galacto-nojirimycin 4).

EXAMPLE 1

Methyl-2,3,4,6-tetra-O-acetyl-L-arabino-5-hexulosonic acid oxime. 5 The ketoaldonic acid 4 (7 g, 18.61 mmol) was dissolved in pyridine (16 ml) and the solution cooled to 0° C. Hydroxylamine hydrochloride (2 g, 28.77 mmol) was then added and the solution stirred at 0° C. for 15 minutes and then for another 2 hours at room temperature. The mixture was poured onto ice and water and then extracted three times with chloroform. The combined chloroform layers were subsequently washed with water, dried with $Na_2SO_4$ and then evaporated. Crystallization from hot ethanol gave white crystals of the oxime (85%) as a mixture of cis-trans isomers: $^1H$ NMR ($CDCl_3$) δ isomer 1:1.98 (s, 3H, OAc), 2.01 (s, 3H, OAc), 2.08 (s, 3H, OAc), 2.15 (S, 3H, OAc), 3.70 (s, 3H, $OCH_3$), 4.82 (d, 1H, $J_{6a,6b}$ 14.6 Hz, H6-a), 5.11 (d, 1H, H6-b), 5.35 (d, 1H, $J_{3,4}$ 1.9 Hz, H-4), 5.68 (d, 1H, $J_{3,2}$ 9.0, Hz, H-2), 5.84 (dd, 1H, H-3); $^{13}C$ NMR ($CDCl_3$) δ20.2, 20.3, 20.4, 20.5, 52.6, 56.4, 68.7, 69.2, 69.6, 149.9, 167.5, 168.9, 169.3, 170.0, 170.3.

EXAMPLE 2

1,5-imino-1,5,6-trideoxy-D-galactito (dideoxy-D-galacto)nojirimycin. 7 This was prepared from the oxime 5 (7.4 g, 18.92 mmol) by reduction with hydrogen on palladium in acetic acid. The intermediate amino ester was cyclized to form a lactam 6 that was then reduced by borane. Flash column chromatography using a chloroform-methanol (6:1) mixture gave (dideoxy-D-galacto)nojirimycin 7 (1.5 g, 30%): $[\alpha]^{23}D+27.0°$© 1.3, $CHCl_3$), lit. +49.0°©1, $CHCl_3$) [20]; $^1H$ NMR ($D_2O$) δ1.21 (d, 3H, $J_{5,6}$ 6.6 Hz, H-6), 2.73 (t, 1H, $J_{1a,1e}$=$J_{1a,2}$ 11.9 Hz, H-1a), 3.30 (dd, 1H, $J_{1e,2}$ 5.4 Hz, H-1e), 3.37 (m, 1H, H-5), 3.50 (dd, 1H, $J_{2,3}$ 9.6 Hz, $J_{3,4}$ 3.1 Hz, H-3), 3.90 (d, 1H, $J_{4,5}$ 3.1 Hz, H-4), 3.91 (ddd, 1H, H-2); $^{13}C$ NMR ($D_2O$) δ14.2, 46.1, 55.0, 64.4, 69.9, 73.1.

Figure 2:
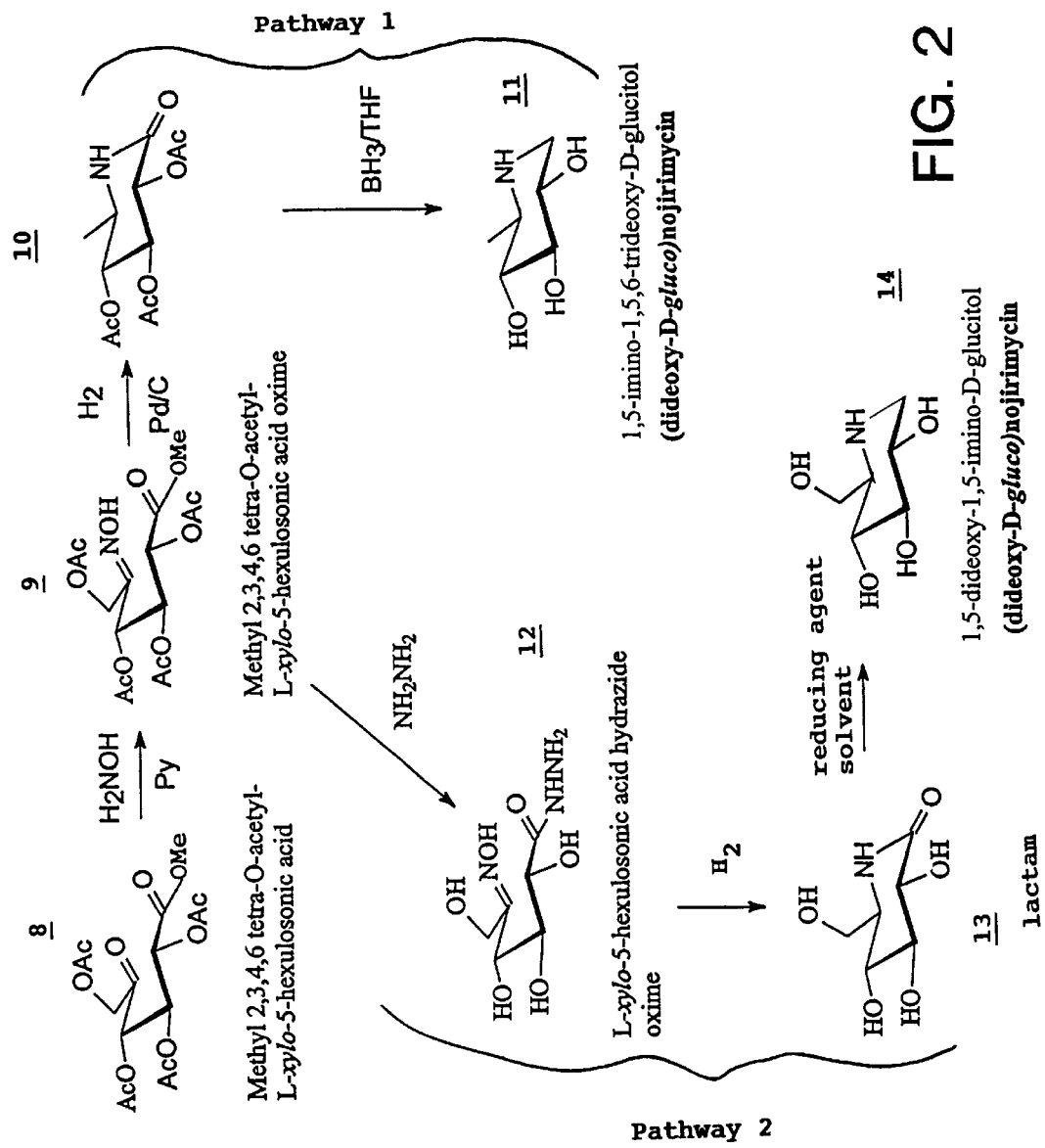
FIG. 2 is a drawing showing the schematic reactions of the reactions of Examples 3 to 6. The numbers are for structures of the compounds of these Examples.

Methyl-2,3,4-6-tetra-O-acetyl-D-xylo-5-hexulosonic acid oximes are intermediates for the preparation of di and tri-deoxynojirimycins. The present invention provides a general method for the preparation of 1,5-imino-1,5-6, trideoxy alditols with the D-gluco configurations starting from the previously unreported methyl-2,3,4,6-tetra-O-acetyl-D-xylo-5-hexulosonic acid oxime 9 (FIG. 2). The key steps are the selective reduction of the oxime derivatives to lactams which are further reduced to the target compounds. The C6 position can be deoxygenated during the reduction if it bears an acetoxy group. The trideoxy imino sugars are then produced. Deacetylation prior to oxime reduction gives the dideoxy compounds.

The present invention provides a simple access to D-gluco nojirimycins from the new oxime intermediate Methyl-2,3, 4,6-tetra-O-acetyl-L-arabino-5-hexulosonic acid oxime. The method also allows access to the 5-amino-5-deoxy-D-glucuronic acid δ-lactams. This also is known from the oxidation of nojirimycin (Kajimoto, T., et al., J. Am. Chem. Soc. 113 6187–6196 (1991)). It is an excellent glycosidase inhibitor at concentrations 100 times lower than most of the other inhibitors tested (Kajimoto, T., et al., J. Am. Chem. Soc. 113 6187–6196 (1991)). In the method we describe here the ketoaldonic acid methyl ester is converted to the previously unreported oxime which is then reduced to the amine which cyclizes to give the lactam. The lactam is reduced to the imino sugar by borane or a metal hydride reagent. (Pathway 1). Despite the formation of both the cis- and trans oximes, no L-derivatives are formed. Reduction of the peracetylated oxime leads to deoxygenation of the 6 position to give the tri-deoxydiiminoalditol (dideoxy-D-gluco-nojirimycin) 14. Access to the 6-hydroxy derivatives was readily achieved by deacetylating the oxime with hydrazine prior to reduction. The deacetylation yielded the acyl hydrazide in quantitative yield (Pathway 2).

EXAMPLE 3

Methyl-2,3,4,6-tetra-O-acetyl-D-xylo-5-hexulosonic acid oxime. 9 The ketone 8 (7 g, 18.61 mmol) was dissolved in pyridine (16 ml) and the solution cooled to 0° C. Hydroxylamine hydrochloride (2 g, 28.77 mmol) was then added and the solution stirred at 0° C. for 15 minutes and then for another 2 hours at room temperature. The mixture was poured onto ice and water and then extracted three times with chloroform. The combined chloroform layers were subsequently washed with water, dried with $Na_2SO_4$ and then evaporated. Crystallization from hot ethanol gave white crystals of the oxime 9 (6.9 g, 95%) as a 3:2 mixture of cis-trans isomers: Isomer 1: $^1H$ NMR ($CDCl_3$) δ1.93 (s, 3H, OAc), 1.94 (s, 3H, OAc), 2.00 (s, 3H, OAc), 2.01 (s, 3H, OAc), 3.56 (s, 3H, $OCH_3$), 4.36 (d, 1H, $J_{6a,6b}$ 12.4 Hz, H6-a), 4.72 (d, 1H, H6-b), 4.99 (d, 1H, $J_{3,4}$ 2.6 Hz, H-4), 5.72 (dd, 1H, $J_{3,2}$ 7.8 Hz, H-3), 6.28 (d, 1H, H-2); $^{13}C$ NMR ($CDCl_3$) δ20.5, 20.4, 52.8, 61.3, 66.1, 69.5, 69.8, 149.9, 167.3, 169.4, 169.5, 170.1; HRMS (M+H$^+$) calcd. 392.1193, found 392.1198. Isomer 2: mp=121–122° C.; $^1H$ NMR ($CDCl_3$) δ1.88 (s, 3H, OAc), 1.89 (s, 3H, OAc), 1.98 (s, 3H, OAc), 2.00 (s, 3H, OAc), 3.56 (s, 3H, $OCH_3$), 4.82 (s, 2H, H-6), 5.16 (d, 1H, $J_{3,4}$ 2.6 Hz, H-4), 5.62 (d, 1H, $J_{3,2}$ 8.5, H-2), 5.78 (dd, 1H, H-3); $^{13}C$ NMR ($CDCl_3$) δ20.5, 20.4, 52.8, 61.3, 66.1, 69.5, 69.8, 149.9, 167.3, 169.4, 169.5, 170.1.

EXAMPLE 4

Tri-O-acetyl-5-amino-5,6-dideoxy-D-gluconic acid lactam. 10 A solution of oxime 9 (6.9, g, 17.64 mmol) in glacial acetic acid (275 ml), containing 10% Pd/C (2.76 g) was hydrogenated in a Parr reactor under a $H_2$ pressure of 300–400 psi for 40 hours at 55° C. The reaction mixture was filtered through celite and washed with ethanol. The solvent was rotary-evaporated and the lactam 10 (5 g, 100%) was obtained as a light yellow syrup: $[\alpha]^{23}$ D+70.0°©1.56, CHCl$_3$); $^1$H NMR (CDCl$_3$) δ1.11 (d, 3H, J$_{5,6}$ 6.3 Hz, H-6), 1.94 (s, 3H, OAc), 1.98 (s, 3H, OAc), 2.00 (s, 3H, OAc), 3.51 (m, 1H, J$_{4,5}$ 9.7, Hz, H-5), 4.94 (t, 1H, J$_{3,4}$ 9.7 Hz, H-3), 4.96 (d, 1H, H-2), 5.40 (t, 1H, H-4); $^{13}$C NMR (CDCl$_3$) δ18.0, 20.3, 20.3, 48.7, 70.6, 70.9, 71.4, 166.7, 169.4, 169.6, 169.8; HRMS (M+H$^+$) calcd. 288.1083, found 288.1089.

EXAMPLE 5

1,5-imino-1,5,6-trideoxy-D-glucitol 11 1M BH$_3$/THF (50 ml, 50 mmol) was added under N$_2$ to a solution of lactam 10 (5 g, 17.41 mmol) in THF (33 ml). The mixture was stirred at room temperature for 1.5 hours and then refluxed for another 1.5 hour. After cooling to room temperature 9% methanolic HCl (40 ml) was carefully added and the resulting solution was refluxed for 30 minutes. The THF was removed by rotary evaporation and the reaction mixture was dissolved repeatedly in methanol, followed by evaporation to remove borates. Water was added to the dry crude product 10 and the solution was passed through an anion exchange resin (Amberlite IR-45 OH-form) and then dried on the rotary evaporator. To remove the last traces of borates, a solution of 1M NaOH (15 mol) and methanol (6 ml) were added to the crude product and the mixture was stirred overnight at room temperature. The methanol was evaporated and the aqueous solution was lyophilized. A methanolic HCl solution was added, which precipitated NaCl while the methanolic solution was dried, to give the product 10 (2.43 g, 95%): [α]$^{23}$D+15.5°©1.88, H$_2$O), lit. +13.°©1.0, H$_2$O)[18]; $^1$H NMR (D$_2$O) δ1.25 (d, 3H, J$_{5,6}$ 6.3 Hz, H-6), 2.77 (dd, 1H, J$_{1a,1e}$ 12.4 Hz, J$_{1a,2}$ 11.7 Hz, H-1a), 3.02 (dd, 1H, J$_{4,5}$ 10.0 Hz, H-5), 3.23 (dd, 1H, J$_{3,4}$ (dd, 1H, J$_{3,4}$ 9.0 Hz, H-4), 3.33 (dd, 1H, J$_{1e,2}$ 5.1 Hz, H-1e), 3.31 (dd, 1H, J$_{2,3}$ 9.2 Hz, H-3), 3.63 (ddd, 1H, H-2); $^{13}$C NMR (D$_2$O) δ17.5, 49.5, 55.2, 71.4, 76.7, 79.0.

EXAMPLE 6

Tetra-O-acetyl-5-amino-5-deoxy-gluconic acid lactam. 13 The acetylated oxime 9 (1.5 g, 3.84 mmol) was deacetylated with concomitant conversion to the acyl hydrazide by treatment with anhydrous hydrazine (0.75 ml, 23.89 mmol) in methanol (15 ml) at room temperature for 2 hours. Evaporation of the solvent gave the crude acid hydrazide 12: $^1$H NMR (D$_2$O) δ4.18 (1H, dd, J=4.6 Hz, J=7.0 Hz) 4.51 (1H, d, J=6.5 Hz), 4.43 (1H, d, J=14.9 Hz), 4.53 (1H, d, J=14.8 Hz), 5.18 (1H, d, J=4.6 Hz); $^{13}$C NMR (D$_2$O) δ61.1, 69.1, 73.4, 73.5, 160.7, 173.4. This hydrazide 12 was hydrogenated in glacial acetic acid with 10%, Pd/C (0.4 g) at 50° C. and 300 psi pressure of H$_2$ for 2 days. After filtration through celite, the solution was dried on the rotary evaporator and the crude product acetylated with acetic anhydride (15 ml) and pyridine (15 ml) for 5 hours at room temperature. The mixture was poured into cold water and extracted with chloroform. The chloroform layer was dried with Na$_2$SO$_4$. Evaporation of the solvent gave crude product 13 (1.47 g), which was subjected to flash chromatography on silica (eluent hexane-acetone=2:1) to give the perahydroxy lactam 13 (0.5 g) C-5 epimer: mp=177–178° C.; [α]$^{23}$D+ 88.6°© 1.11, CHCl$_3$), lit. +104°©1.73, CHCl$_3$) [17]; $^1$H NMR (CDCl$_3$) δ2.03 (s, 3H, OAc), 2.06 (s, 3H, OAc), 2.08 (s, 3H, OAc), 2.10 (s, 3H, OAc), 3.75 (ddd, 1H, J$_{4,5}$ 9.7 Hz, J$_{5,6a}$ 2.9 Hz, J$_{5,6b}$ 6.5 Hz, H-5), 3.96 (dd, 1H, J$_{6a,6b}$ 11.7 Hz, H6-b), 4.22 (dd, 1H, H-6a), 5.06 (d, 1H, J$_{3,2}$ 9.5 Hz, H-2), 5.20 (t, 1H, J$_{3,4}$ 9.5 Hz, H-3), 5.53 (dd, 1H, H-4), 6.48 (s, 1H, s, NH); $^{13}$C NMR (CDCl$_3$) δ20.5, 20.5, 20.5, 20.6, 52.4, 62.7, 67.2, 70.4, 70.5, 166.2, 169.4, 169.6, 170.0, 170.4 HRMS (M+H$^+$) calcd. 346.1060, found 346.1143.

Epimer: [α]$^{23}$D+3.1°©1.81, CHCl$_3$); $^1$H NMR (CDCl$_3$) 1.98 (s, 3H, OAC), 1.99 (s, 3H, (OAC), 2.00 (2, 3H, OAC), 2.02 (s, 3H, OAC), 3.88 (1H, m, H-5), 4.04 (dd, 1H, J$_{6a,6b}$ 11.4 Hz, J$_{5,6b}$ 6.3 Hz, H6-b), 4.18 (dd, 1H, J$_{5,6a}$ 3.9 Hz, H-6a), 5.15 (dd, 1H, J$_{4,5}$ 9.5 Hz, J$_{3,4}$ 7.5 Hz, H-4), 5.15 (d, 1H, J$_{2,3}$ 7.5 Hz, H-2), 5.39 (t, 1H, H-3), 7.27 (1H, s, broad, NH); $^{13}$C NMR (CDCl$_3$) δ20.2, 20.3, 20.4, 50.0, 62.0, 68.0, 69.8, 70.0, 166.7, 169.3, 169.7, 170.3, 170.6. The lactam 13 was converted to the 1,5-diamino-1,5-dideoxy-D-glucitol (dideoxy-D-gluco)nojuirmycin 14 as in Example 5.

Figure 3:
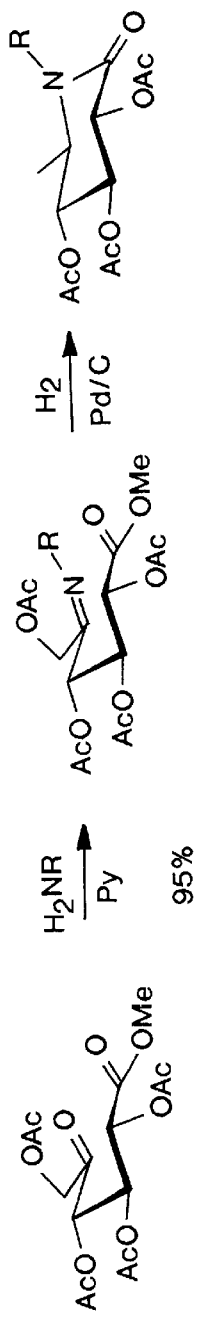
FIG. 3 is a drawing showing the reactions where an oxime group is replaced with an imino alkyl group.
Figure 4:
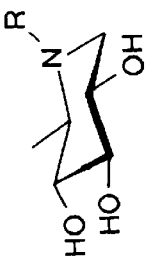
FIG. 4 is a drawing showing the reaction of the hexitol with an aldehyde to produce an alkyl group on the nitrogen.
Figure 4:
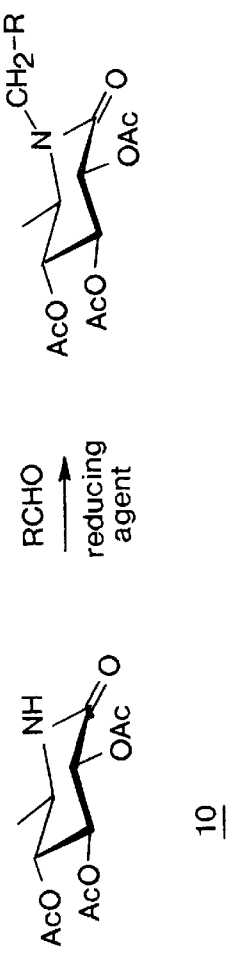

It will be appreciated that the imino group can contain a lower alkyl group containing 1 to 6 carbon atoms rather than hydrogen. The oxime group in compound 5 would then be an imino alkyl group, preferably where alkyl contains 1 to 8 carbon atoms. The reactions are shown in FIG. 3. The hydrogen on the hexitol can be replaced with an alkyl group by reaction with an alkyl aldehyde and a reducing agent as shown in FIG. 4.

It is intended that the foregoing description be only illustrative of the present invention and that the present invention be limited only by the hereinafter appended claims.

We claim:
1. Methyl-2,3,4,6-tetra-O-acetyl-L-arabino-5-hexulosonic acid oxime.
2. Methyl-2,3,4,6-tetra-O-acetyl-D-xylo-5-hexulosonic acid oxime.
3. Methyl-2,3,4,6-tetra-O-acetyl-L-xylo-5-hexulosonic acid hydrazide oxime.

* * * * *